(12) United States Patent
Siejko et al.

(10) Patent No.: US 10,195,443 B2
(45) Date of Patent: *Feb. 5, 2019

(54) SYSTEMS AND METHODS FOR RANKING AND SELECTION OF PACING VECTORS

(71) Applicant: Cardiac Pacemakers, Inc., St. Paul, MN (US)

(72) Inventors: Krzysztof Z. Siejko, Maple Grove, MN (US); Shibaji Shome, Arden Hills, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 211 days.

This patent is subject to a terminal disclaimer.

(21) Appl. No.: 15/210,342

(22) Filed: Jul. 14, 2016

(65) Prior Publication Data

US 2016/0317818 A1 Nov. 3, 2016

Related U.S. Application Data

(63) Continuation of application No. 14/520,559, filed on Oct. 22, 2014, now Pat. No. 9,393,426, which is a
(Continued)

(51) Int. Cl.
*A61N 1/37* (2006.01)
*A61N 1/05* (2006.01)
(Continued)

(52) U.S. Cl.
CPC .......... *A61N 1/3704* (2013.01); *A61N 1/056* (2013.01); *A61N 1/368* (2013.01); *A61N 1/3686* (2013.01);
(Continued)

(58) Field of Classification Search
CPC ........ A61N 1/056; A61N 1/36; A61N 1/3605; A61N 1/36185; A61N 1/36514; A61N 1/36585; A61N 1/368; A61N 1/3704
(Continued)

(56) References Cited

U.S. PATENT DOCUMENTS 6,128,535 A 10/2000 Maarse
6,493,586 B1 12/2002 Stahmann et al.
(Continued)

FOREIGN PATENT DOCUMENTS

JP 2009513251 A 4/2009
WO WO-2007053298 A2 5/2007
(Continued)

OTHER PUBLICATIONS

"U.S. Appl. No. 12/822,487, Advisory Action dated Feb. 12, 2013", 3 pgs.
(Continued)

*Primary Examiner* — Christopher A Flory
(74) *Attorney, Agent, or Firm* — Schwegman Lundberg & Woessner, P.A.

(57) ABSTRACT

Approaches to rank potential left ventricular (LV) pacing vectors are described. Early elimination tests are performed to determine the viability of LV cathode electrodes. Some LV cathodes are eliminated from further testing based on the early elimination tests. LV cathodes identified as viable cathodes are tested further. Viable LV cathode electrodes are tested for hemodynamic efficacy. Cardiac capture and phrenic nerve activation thresholds are then measured for potential LV pacing vectors comprising a viable LV cathode electrode and an anode electrode. The potential LV pacing vectors are ranked based on one or more of the hemodynamic efficacy of the LV cathodes, the cardiac capture thresholds, and the phrenic nerve activation thresholds.

20 Claims, 5 Drawing Sheets

Related U.S. Application Data continuation of application No. 12/822,487, filed on Jun. 24, 2010, now Pat. No. 8,886,313.

(60) Provisional application No. 61/222,745, filed on Jul. 2, 2009.

(51) Int. Cl.
    *A61N 1/36* (2006.01)
    *A61N 1/365* (2006.01)
    *A61N 1/368* (2006.01)

(52) U.S. Cl.
    CPC ..... *A61N 1/36185* (2013.01); *A61N 1/36514* (2013.01); *A61N 1/36542* (2013.01); *A61N 1/36585* (2013.01); *A61N 1/371* (2013.01)

(58) Field of Classification Search
    USPC .................. 607/9, 27, 28; 600/509, 512
    See application file for complete search history.

(56) References Cited

U.S. PATENT DOCUMENTS

| | | |
|---|---|---|
| 6,615,089 B1 | 9/2003 | Russie et al. |
| 6,760,622 B2 | 7/2004 | Helland et al. |
| 6,937,901 B2 | 8/2005 | Zhu et al. |
| 6,978,178 B2 | 12/2005 | Sommer et al. |
| 7,031,773 B1 | 4/2006 | Levine et al. |
| 7,130,682 B2 | 10/2006 | Stahmann et al. |
| 7,225,035 B2 | 5/2007 | Brabec et al. |
| 7,299,093 B2 | 11/2007 | Zhu et al. |
| 7,392,086 B2 | 6/2008 | Sathaye |
| 7,412,287 B2 | 8/2008 | Yonce et al. |
| 7,509,170 B2 | 3/2009 | Zhang et al. |
| 7,630,763 B2 | 12/2009 | Kwok et al. |
| 7,697,985 B2 | 4/2010 | Kaiser et al. |
| 7,908,004 B1 | 3/2011 | Gill et al. |
| 7,945,325 B2 | 5/2011 | Stahmann et al. |
| 8,014,860 B2 | 9/2011 | Kwok et al. |
| 8,589,123 B2 | 11/2013 | Uraki et al. |
| 8,886,313 B2 | 11/2014 | Siejko et al. |
| 9,393,426 B2 | 7/2016 | Siejko et al. |
| 2003/0204232 A1 | 10/2003 | Sommer et al. |
| 2005/0060009 A1 | 3/2005 | Goetz |
| 2006/0142814 A1 | 6/2006 | Laske et al. |
| 2006/0155202 A1 | 7/2006 | Arand et al. |
| 2006/0155338 A1 | 7/2006 | Mongeon et al. |
| 2006/0253162 A1 | 11/2006 | Zhang et al. |
| 2006/0253164 A1 | 11/2006 | Zhang et al. |
| 2007/0027488 A1 | 2/2007 | Kaiser et al. |
| 2007/0032733 A1 | 2/2007 | Burton |
| 2007/0066998 A1 | 3/2007 | Hansen et al. |
| 2007/0129762 A1 | 6/2007 | Worley |
| 2008/0004674 A1 | 1/2008 | King et al. |
| 2008/0004675 A1 | 1/2008 | King et al. |
| 2008/0046036 A1 | 2/2008 | King et al. |
| 2008/0071318 A1 | 3/2008 | Brooke et al. |
| 2008/0177344 A1 | 7/2008 | Maskara et al. |
| 2008/0294215 A1 | 11/2008 | Sathaye |
| 2008/0294218 A1 | 11/2008 | Savage et al. |
| 2008/0300644 A1 | 12/2008 | Sathaye |
| 2008/0306567 A1 | 12/2008 | Park et al. |
| 2009/0043351 A1 | 2/2009 | Sathaye et al. |
| 2009/0043352 A1 | 2/2009 | Brooke et al. |
| 2009/0210024 A1 | 8/2009 | Brooke |
| 2010/0114227 A1 | 5/2010 | Cholette et al. |
| 2011/0004264 A1 | 1/2011 | Siejko et al. |
| 2011/0092809 A1 | 4/2011 | Nguyen et al. |
| 2015/0039044 A1 | 2/2015 | Siejko et al. |

FOREIGN PATENT DOCUMENTS

| | | |
|---|---|---|
| WO | WO-2008005142 A1 | 1/2008 |
| WO | WO-2009020639 A1 | 2/2009 |
| WO | WO-2011002671 A1 | 1/2011 |

OTHER PUBLICATIONS

"U.S. Appl. No. 12/822,487, Decision on Pre-Appeal Brief Request mailed May 17, 2013", 3 pgs.
"U.S. Appl. No. 12/822,487, Examiner Interview Summary dated Jan. 2, 2013", 4 pgs.
"U.S. Appl. No. 12/822,487, Examiner Interview Summary dated Jan. 29, 2014", 4 pgs.
"U.S. Appl. No. 12/822,487, Examiner Interview Summary dated Jun. 3, 2014", 4 pgs.
"U.S. Appl. No. 12/822,487, Final Office Action dated May 1, 2014", 10 pgs.
"U.S. Appl. No. 12/822,487, Final Office Action dated Nov. 20, 2012", 9 pgs.
"U.S. Appl. No. 12/822,487, Non Final Office Action dated Jul. 23, 2012", 10 pgs.
"U.S. Appl. No. 12/822,487, Non Final Office Action dated Nov. 27, 2013", 13 pgs.
"U.S. Appl. No. 12/822,487, Notice of Allowance dated Jul. 3, 2014", 5 pgs.
"U.S. Appl. No. 12/822,487, Pre-Appeal Brief Request filed Mar. 13, 2013", 8 pgs.
"U.S. Appl. No. 12/822,487, Response filed Jan. 4, 2013 to Final Office Action dated Nov. 20, 2012", 11 pgs.
"U.S. Appl. No. 12/822,487, Response filed Feb. 27, 2014 to Non Final Office Action dated Nov. 27, 2013", 12 pgs.
"U.S. Appl. No. 12/822,487, Response filed May 18, 2012 to Restriction Requirement dated Apr. 18, 2012", 8 pgs.
"U.S. Appl. No. 12/822,487, Response filed Jun. 13, 2014 to Final Office Action dated May 1, 2014", 11 pgs.
"U.S. Appl. No. 12/822,487, Response filed Jun. 17, 2013 to Decision on Pre-Appeal Brief Request dated May 17, 2013", 12 pgs.
"U.S. Appl. No. 12/822,487, Response filed Oct. 23, 2012 to Non Final Office Action dated Jul. 23, 2012", 13 pgs.
"U.S. Appl. No. 12/822,487, Restriction Requirement dated Apr. 18, 2012", 8 pgs.
"U.S. Appl. No. 14/520,559, Non Final Office Action dated Oct. 16, 2015", 14 pgs.
"U.S. Appl. No. 14/520,559, Notice of Allowance dated Mar. 18, 2016", 11 pgs.
"U.S. Appl. No. 14/520,559, Response filed Jan. 14, 2016 to Non Final Office Action dated Oct. 16, 2015", 8 pgs.
"European Application Serial No. 10729747.5, Decision to Grant dated Oct. 5, 2012", 2 pgs.
"European Application Serial No. 10729747.5, Intention to Grant dated May 21, 2012", 38 pgs.
"International Application Serial No. PCT/US2010/039915, International Preliminary Report on Patenabilty dated Jan. 12, 2012", 9 pgs.
"International Application Serial No. PCT/US2010/039915, International Search Report dated Sep. 1, 2010", 4 pgs.
"International Application Serial No. PCT/US2010/039915, Written Opinion dated Sep. 1, 2010", 7 pgs.
"Japanese Application No. 2012-518558, Office Action dated Apr. 23, 2013", 6 pgs.
"Germany Application Serial No. 10729747.5, Office Action dated Apr. 23, 2013", 7 pgs.

SYSTEMS AND METHODS FOR RANKING AND SELECTION OF PACING VECTORS

RELATED PATENT DOCUMENTS

This application is a Continuation of U.S. patent application Ser. No. 14/520,559 filed on Oct. 22, 2014, now issued as U.S. Pat. No. 9,393,426, which is a Continuation of U.S. patent application Ser. No. 12/822,487 filed on Jun. 24, 2010, now issued as U.S. Pat. No. 8,886,313, which claims the benefit of Provisional Patent Application Ser. No. 61/222,745, filed on Jul. 2, 2009, the entire contents of which are incorporated herein by reference.

FIELD OF THE INVENTION

The present invention relates generally to cardiac devices and methods, and, more particularly, to ranking potential pacing electrode vectors used for pacing the heart.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management (CRM) devices have been developed that provide pacing stimulation to one or more heart chambers in an attempt to improve the rhythm and coordination of atrial and/or ventricular contractions. CRM devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dyssynchrony. Pacemakers are CRM devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue, generating an evoked response that generates a propagating depolarization wave that results in a contraction of the heart chamber. It is desirable for a pace pulse to have sufficient energy to stimulate capture of the heart chamber without expending energy significantly in excess of the capture threshold. Pacing in excess of a capture threshold can cause excessive energy consumption, require premature battery replacement, and can unintentionally stimulate nerves or muscles. However, if a pace pulse energy is too low, the pace pulses may not reliably produce a contractile response in the heart chamber and may result in ineffective pacing that does not improve cardiac function or cardiac output.

Electrical cardiac therapies include other complexities. For example, low impedance between an anode and cathode pair can require excessive energy delivery, causing high energy consumption and prematurely depleting the battery resources. In another example, excessively high impedance between an anode and cathode pair indicates a problem with the stimulation circuit (i.e. lead damage), resulting in a lack of therapy.

Delivering electrical cardiac therapy may involve selection of an electrode combination to which the electrical cardiac therapy is delivered. Devices for cardiac pacing and sensing may utilize a number of electrodes electrically coupled to the heart at one or more pacing sites, the electrodes configured to sense and/or pace a heart chamber. Each different combination of electrodes between which energy can be delivered constitutes a vector. Pacing via multiple intra-chamber electrode pairs may be beneficial, for example, to stimulate the heart tissue in a coordinated sequence that improves contractile function of the heart chamber.

The present invention provides methods and systems for selecting an electrode combination and provides various advantages over the prior art.

SUMMARY OF THE INVENTION

Embodiments of the present invention involve approaches for ranking and/or selecting one or more pacing vectors. One embodiment is directed to an automated method of operating a cardiac device to rank potential pacing vectors. One or more parameter values indicative of pacing viability are measured for a plurality of cathode electrodes. A set of cathode electrodes are identified as viable cathode electrodes based on the measured parameter values. At least some of the cathode electrodes are eliminated from further testing based on the measured parameter values. After the viable cathode electrodes are identified for further testing, a parameter indicative of hemodynamic function is measured for at least some of the viable cathode electrodes.

Cardiac capture threshold and/or phrenic nerve activation threshold are measured for potential LV pacing vectors comprising a viable cathode electrode and an anode electrode. The potential pacing vectors are ranked based on one or more of the value of the hemodynamic function parameter, the cardiac capture threshold and the phrenic nerve activation threshold. An output is generated by the cardiac device based on the ranking.

According to one implementation, ranking the potential pacing vectors involves ranking the potential pacing vectors in multiple tiers. One tier may rank the viable cathode electrodes based on the hemodynamic function parameter value and another tier may rank the potential pacing vectors based on one or more of the capture threshold value and the phrenic nerve activation threshold value. The potential pacing vectors may also be ranked based on pacing impedance, signal amplitude values, and/or anodal stimulation threshold values.

Measuring the parameter values indicative of pacing viability may involve measuring intrinsic values such as signal amplitude or pacing impedance. Additionally or alternatively, paced characteristics such as cardiac capture or phrenic nerve activation may be tested and/or measured.

According to some implementations, the parameter associated with hemodynamic function is the cardiac electrical signal propagation delay associated with a viable left ventricular (LV) cathode electrode. For example, the propagation delay may be measured between a right chamber event and detection of an LV depolarization responsive to the right chamber event at the viable LV cathode electrode.

The propagation delay and/or other parameters may be extrapolated or interpolated for a particular cathode based on the measured values of nearby cathodes. Alternatively, a cathode may not be tested if a nearby cathode is determined to be a non-viable cathode.

According to one implementation, a set of hemodynamically preferred LV cathode electrodes is determined based on measured hemodynamic function values. LV cathode electrodes that are associated with phrenic nerve activation are eliminated if they are not included within the set of hemodynamically preferred of LV cathode electrodes.

Not all potential cathode electrodes or pacing vectors may be tested. For example, potential cathodes or vectors that are undesirable for some reason, or are not among the commonly used cathodes or vectors, may be eliminated from the test. Cathodes and/or pacing vectors that are not desirable for use and/or that are not commonly used may identified by the patient's physician via a user input, or automatically by the cardiac device based on physician survey information and/or data mining which is available via an advanced patient management (APM) server.

According to some aspects of the invention one or more potential LV pacing vectors, e.g., the extended bipolar vectors, may be monitored for anodal stimulation. The anodal stimulation information including presence of anodal stimulation and/or anodal stimulation threshold values may be used for ranking and/or may be stored and/or presented to the physician along with the ranking for the LV pacing vector.

In some implementations, a pacing vector may be eliminated from further testing if the vector is determined to be sufficiently close to an infarct site.

Another embodiment of the invention is directed to a cardiac device that is configured to rank potential pacing vectors. The device includes a plurality of implantable electrodes electrically coupled to a heart. The cardiac device may include fully implantable circuitry coupled to the cardiac electrodes, or a patient-external pacing system analyzer which is coupled to the implantable cardiac electrodes. In some embodiments, the functions of the cardiac device may be divided between implanted and patient-external circuitry.

Arranged within the cardiac device is circuitry configured to measure one or more parameter values for a plurality of cathode electrodes and, based on the measured parameter values, to identify for further testing a set of cathode electrodes as viable cathode electrodes. One or more non-viable cathode electrodes are eliminated from further testing. Also included is a hemodynamic function module configured to test the hemodynamic function of pacing using at least some of the viable cathode electrodes. A threshold test module measures one or more of cardiac capture threshold and phrenic nerve activation threshold for potential pacing vectors, where each potential pacing vector is defined between a viable cathode electrode and an anode electrode. A ranking module ranks the potential pacing vectors based on one or more of the hemodynamic efficacy of the cathode electrodes, the measured capture threshold values of the potential LV pacing vectors, and the measured phrenic nerve activation threshold values of the LV pacing vectors. An output is generated based on the ranking.

For patient-external circuitry implementations, the cardiac device may include a patient-external accelerometer e.g., attached to the patient near the diaphragm, which is configured to sense phrenic nerve activation. The cardiac device may include a subcutaneous electrode disposed on a lead that simulates a can electrode of a cardiac rhythm management device.

The cardiac device may also include a user interface configured to receive an input from a user. Ranking the potential pacing vectors can be based at least in part on the user input. The user interface may generate text or graphics to display the ranking of the potential LV pacing vectors. A physician or other analyst can input information to the cardiac device via the user interface to control the ranking or re-ranking of the pacing vectors.

Other embodiments of the invention are directed to the identification of electrodes which are proximate to, e.g., near or above, an infarct site. The identification of the electrodes proximate to the infarct site may be used in ranking the potential pacing vectors. The approach involves measuring an intrinsic signal amplitude and cardiac capture threshold of a group of pacing electrodes. Circuitry identifies one or more electrodes as proximate to the infarct region based on their intrinsic signal amplitude and the cardiac capture threshold relative to the intrinsic signal amplitude and cardiac capture threshold of other electrodes of the group. For example, the one or more electrodes near the infarct site may be identified if the one or more electrodes have higher cardiac capture thresholds and similar signal amplitudes when compared to other electrodes of the group.

The above summary is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
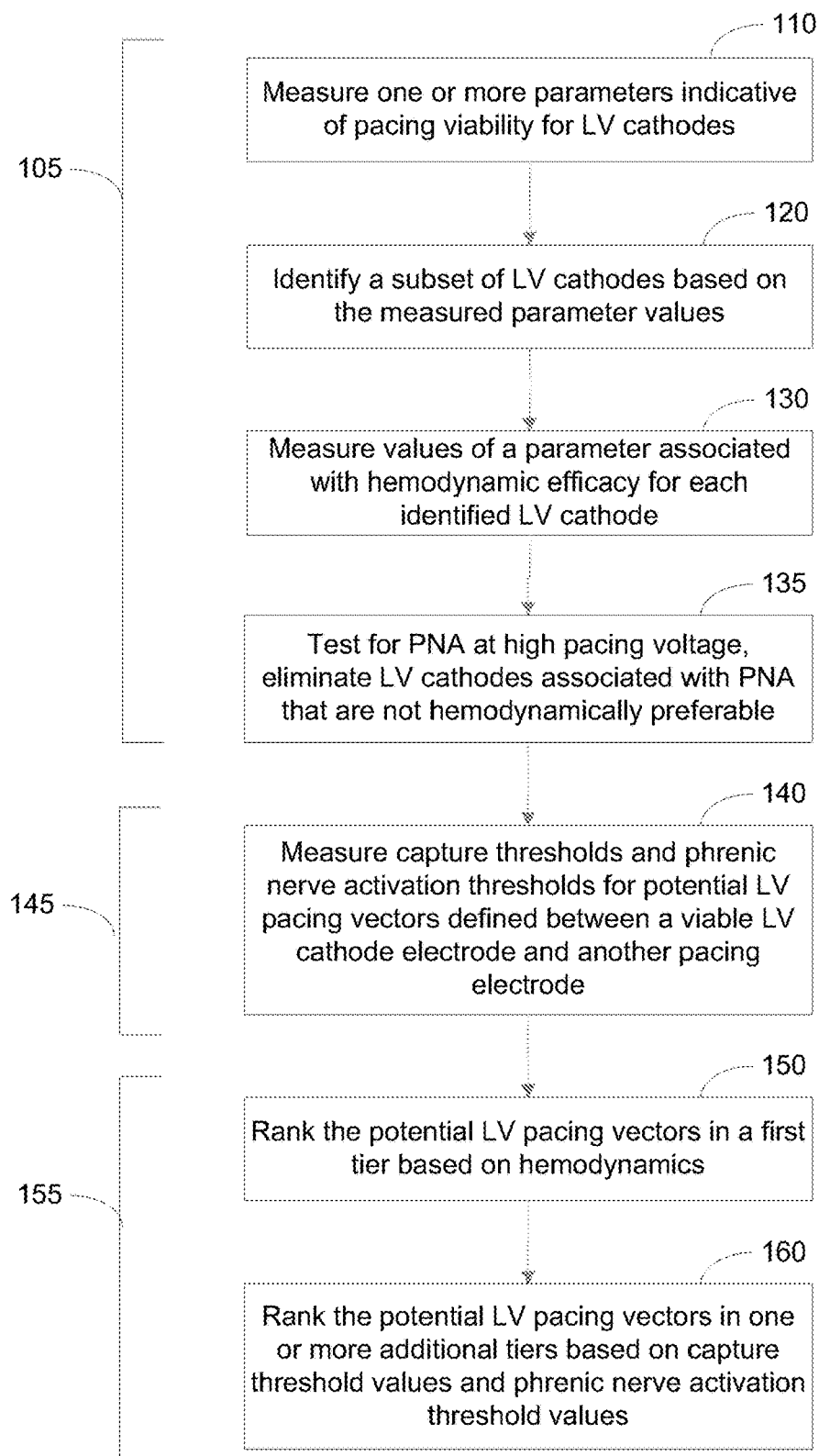
FIG. 1 is a flow diagram that illustrates pacing vector testing and ranking processes in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The discussion and illustrations provided herein are presented in an exemplary format, wherein selected embodiments are described and illustrated to present the various aspects of the present invention. Systems, devices, or methods according to the present invention may include one or more of the features, structures, methods, or combinations thereof described herein. For example, a device or system may be implemented to include one or more of the advantageous features and/or processes described below. A device or system according to the present invention may be implemented to include multiple features and/or aspects illustrated and/or discussed in separate examples and/or illustrations. It is intended that such a device or system need not include all of the features described herein, but may be implemented to include selected features that provide for useful structures, systems, and/or functionality.

In multi-electrode pacing systems, multiple pacing electrodes may be disposed in a single heart chamber, in multiple heart chambers, and/or elsewhere in a patient's body. Electrodes used for delivery of pacing pulses may include one or more cathode electrodes and one or more anode electrodes. Pacing pulses are delivered via the cathode/anode electrode combinations, where the term "pacing vector" denotes that at least one cathode electrode and at least one anode electrode are used. A pacing vector may involve more than two electrodes, such as when multiple electrodes that are electrically connected are used as the anode and/or multiple electrodes that are electrically connected are used as the cathode. Typically, pacing energy is delivered to the heart tissue via the cathode electrode(s) at one or more pacing sites, with a return path provided via the anode electrode(s). If capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing. The position of the cathode relative to cardiac tissue can be used to define a pacing vector and/or a pacing site.

Pacing pulses may be applied to a heart chamber via a pacing vector in a timed sequence during the cardiac cycle to improve contractility and enhance the pumping action of the heart chamber. It is generally desirable for each pacing pulse to capture the cardiac tissue proximate the cathode electrode. The pacing energy required to capture the heart is dependent on the vector used for pacing. Different pacing vectors can have different energy requirements for capture. Particularly in the left ventricle, the minimum energy required for capture, denoted the capture threshold, may be highly dependent on the particular electrode combination used. In addition, different pacing vectors may have other differing parameters, such as hemodynamic benefit, undesirable activation of other body structures, sensing amplitude, pacing impedance, etc.

Pacing characteristics of therapy delivery using each pacing vector of a plurality of possible pacing vectors are dependent on many factors, including the distance between the vector electrodes, proximity to target tissue, proximity to non-target tissue, type of tissue contacting and between the electrodes, impedance between the electrodes, resistance between the electrodes, and electrode type, among other factors. Such factors can influence the various parameters associated with pacing or sensing the heart, including the amplitude of the intrinsic cardiac signal sensed using the pacing vector, cardiac capture threshold, extra-cardiac stimulation threshold, anodal stimulation threshold, pacing impedance, and hemodynamic efficacy achieved using the pacing vector, among other parameters. Pacing and/or sensing characteristics can vary with physiologic changes, electrode migration, physical activity level, body fluid chemistry, hydration, and disease state, among others. Therefore, the pacing/sensing characteristics for each pacing vector are unique, and some pacing vectors may work better than others for delivering a particular therapy. Pacing vector selection should take into consideration a variety of pacing characteristics of the potential pacing vectors.

Embodiments of the invention are directed to approaches for more efficient selection of pacing electrode combinations (pacing vectors) for pacing a heart chamber. Although the details of the invention are illustrated using embodiments based on ranking and selection of pacing vectors for left ventricular (LV) pacing, the principles of the invention are also applicable to other cardiac chambers, i.e., left atrium, right ventricle, right atrium. The approaches described enhance the vector selection process by streamlining aspects of the selection process. It will be appreciated that that the use of multi electrode leads provides a significant number of different pacing vectors that could possibly be used to deliver pacing. If performed at the time of implant, or during a follow up visit with a physician, exhaustive testing of each possible combination may be too time consuming to be practical. Exhaustive testing during ambulatory operation may also be undesirable, for example, in situations where the testing interferes with therapy delivery. Therefore, it is advantageous to test the pacing vectors in a way that focuses on the pacing vectors having a higher probability of selection.

The pacing vectors selected for optimal therapy delivery may be different depending on the condition of the patient. For example, some patients may require optimal hemodynamic pumping, and may tolerate a higher incidence of phrenic nerve activation or higher pacing impedance. Other patients may tolerate less than optimal hemodynamic pumping, but are less tolerant to phrenic nerve activation, for example. Thus, it is advantageous for the pacing vector testing to take into account the needs of individual patients to test the potential pacing vectors, to present the test results, and/or to make recommendations for pacing vector selection.

Embodiments of the invention describe enhanced approaches for testing and selecting LV pacing vectors, although the devices and techniques described are also applicable to pacing vector selection for other cardiac chambers. These approaches may be implemented at various times such as during implantation of a cardiac device, during a patient follow-up visit to the physician, and/or as an ambulatory procedure. For example, if implemented during implantation, a patient-external pacing system analyzer (PSA) may perform the vector selection algorithm while attached to implanted leads; if implemented as an ambulatory process, the vector selection algorithm maybe performed by an implanted pacemaker or cardiac resynchronization therapy (CRT) device; if implemented during a follow up visit by an implant patient at a physician's office, the testing may performed under the control of a programmer or other patient-external device.

FIG. 1 is a flow diagram that illustrates automatic pacing vector testing and ranking (AVT) sub-processes in accordance with embodiments of the invention. In an early elimination sub-process 105 that streamlines subsequent testing and ranking of potential LV pacing vectors, LV cathodes which are not viable for use as LV pacing vector cathodes are eliminated from the vector selection process. This portion of the early elimination sub-process 105 may be accomplished by implementing one or more simple tests to determine which, if any, LV cathodes are less viable for pacing. The cathodes may be individual electrodes or may be electrode combinations, i.e., electrodes shorted together to form a multi-electrode cathode. Not all possibilities of individual or multi-electrode LV cathodes may be considered in the AVT process. For example, in the early elimination sub-process 105, the cathodes tested may be pre-selected by a physician, by a patient-external pacing system analyzer, implanted device programmer or advanced patient management server, and/or by the implanted device based on a priori information of the most likely candidate cathodes/electrodes.

For example, the selection of most likely viable cathodes may be made by implant patient's physician using her/his knowledge and analysis of the specific implant patient's condition; may be made automatically by a medical device based on survey information obtained from a number of physicians regarding a similar population of patients, and/or information obtained through bioinformatics analysis, such as mining the database of an advanced patient management (APM) server (also known as a remote patient monitoring (RPM) server). The result of the early elimination testing sub-process 105 is the identification of a set of viable LV cathodes which will be subjected to further testing and elimination from further testing those LV cathodes which are non-viable. The early elimination of non-viable LV cathodes speeds and simplifies the remaining AVT process by focusing the next phases of testing on LV pacing vectors which use those LV cathodes identified as viable.

The early elimination testing 105 involves measuring 110 values of one or more parameters which are indicative of pacing viability. In some scenarios, the initial testing may be based on one or more intrinsic measurements, such as measuring the signal amplitude, e.g., R-wave amplitude or P-wave amplitude, or pacing impedance achieved using the cathode electrode. Testing of intrinsic parameters may be used alone, or in addition to other testing procedures. If the R-wave amplitude is low and/or the pacing impedance is excessively high for a particular LV cathode, this is an indication that LV pacing vectors which use the particular the LV cathode are less likely to be selected.

After testing 110, an initial set of viable LV cathode electrodes is identified 120. In this step, the results of the intrinsic and/or other measurements are compared to an expected range. If the results of the measurements for a particular LV cathode fall outside of an expected range, the LV cathode is eliminated and is not used in further testing.

In some scenarios, the testing for pacing viability 110 may be accomplished using paced characteristics in addition to or as an alternative to the intrinsic measurements. For example, cardiac capture testing using a very limited subset of testing voltages may be used in the initial testing 110 of the early elimination sub-process 105. The anode used with the cathodes being tested may be fixed for all cathodes for the initial viability screening. For example, the can, a right ventricular lead electrode, and/or or coil can be used as the anode. The capture testing may be used alone, or in addition to other testing procedures. If a particular LV cathode fails to produce capture at the limited subset of one or more testing voltages, e.g., capture testing at 5V, and/or if the capture threshold for pacing using the LV cathode is beyond an expected range, then the LV cathode may be eliminated from further testing. The subset of voltages used for capture testing and/or the maximum value of the acceptable capture threshold may be user-defined.

Alternatively, or additionally, hemodynamic function testing may be used in the initial testing 110 of the early elimination sub-process 105. In some configurations LV cathodes that are positioned near an LV cathode which has been screened for hemodynamic function may not be tested. For example, if a hemodynamic function test is performed for one or more LV cathodes positioned in a cardiac region having one or more nearby LV cathodes, the nearby LV cathodes may not need to be tested for hemodynamic function. In one scenario, the measurement for the tested LV cathode may be used to extrapolate or interpolate measurement value(s) for the one more untested LV cathodes in that region. This process eliminates the need for performing hemodynamic function measurements for each LV cathode where an extrapolation or interpolation is sufficient.

In some configurations, if an LV cathode fails an initial test, e.g., a pacing impedance test or an initial capture threshold test, one or more nearby cathodes may also be eliminated and excluded from further testing based on the failure of the nearby LV cathode. The use of measurements of nearby LV cathodes to determine values for or eliminate nearby LV cathodes including the distances between the neighboring LV cathodes for required for extrapolation or interpolation of values, or required for elimination of the LV cathode based on proximity may be programmed into the device and/or may be selectable by a physician.

Following the initial testing involving measuring 110 values of one or more parameters which are indicative of pacing viability, some of the LV cathode electrodes are eliminated from further testing and subset of LV cathode electrodes is identified 120 for further testing. The initial sub-process 105 may also include a second phase of early elimination testing that includes hemodynamic testing 130 of the subset of LV cathodes identified 120 by initial viability testing 110. The subset of LV cathodes is tested to determine hemodynamic differences in pacing using the subset of LV cathodes. In some embodiments, the hemodynamic differences may be identified based on measurements of QRS width, measured LV time delays, and/or LV dp/dt measurements, for example. Hemodynamic function tests can be based on information from external sensors, such as, but not limited to: pressure catheters in any chamber of the heart, in the pulmonary artery, arterial pressure, non-invasive sensors including heart sounds based measurements, echocardiographic measurements, fluoroscopic measurements, finger plethysmography, and/or other parameters which can be used to ascertain hemodynamic differences. Some of the LV cathodes of the identified subset may not be tested in this sub-process. For example, similarly to the procedures of the first phase 110, 120 of early elimination testing, only one or a few of the LV cathode electrodes that are within a cardiac region or predesignated zone may be tested. LV cathodes within the zone are sufficiently close to each other so that they can be considered hemodynamically equivalent. The area of the zone may be defined of modified, for example, by input from a physician. The value(s) obtained by testing one or a few possible LV cathodes in a region may be used to extrapolate or interpolate values for the untested cathodes in that region. In some cases, for LV cathodes within a predetermined distance of each other, it may be assumed that the hemodynamic differences can be ascertained from measurements of nearby cathodes or the differences between the closely spaced cathodes would be inconsequential. Testing of some LV cathodes of the subset may be skipped in the interest of test time efficiency.

The sensed LV time delay is one measurement used to quantify hemodynamic differences between possible LV cathodes. The sensed LV time delay may be measured as the time interval between a reference event and an LV depolarization detected at the cathode under test. The sensed LV time delay may comprise, for example, the time interval between onset of the Q wave to the sensed LV depolarization (Q-LV), the time interval between delivery of a right chamber pacing pulse to the sensed LV depolarization, the time interval between detection of a right chamber evoked depolarization to a sensed LV depolarization, the time interval between an intrinsic right chamber depolarization to a sensed LV depolarization, for example. The right chamber may be the right atrium or the right ventricle. For example, the measurement maybe performed using the timing of right atrial pacing pulse, the timing of an evoked right atrial depolarization, or the timing of a sensed intrinsic right atrial depolarization as the reference event. For patients with AV block, the timing of a right ventricular (RV) pacing pulse, the timing of an evoked RV depolarization, or the timing of an intrinsic RV depolarization may be used as the reference event. If one or more hemodynamically preferable LV cathodes are identified at this step, the presence of low phrenic nerve activation (PNA) threshold and/or high cardiac capture threshold will not necessarily eliminate the hemodynamically preferable cathode electrodes from further consideration.

The early elimination sub-process 105 may also involve testing 135 for the presence of PNA at a relatively high pacing voltage, e.g., about 5 to about 7.5 volts, for the subset of LV cathode electrodes previously identified as viable. LV cathode electrodes that are associated with PNA that are not hemodynamically preferable may be eliminated from the group of viable LV cathodes before additional testing of the LV pacing vectors proceeds. For example, LV cathodes associated with PNA may be required to exhibit superior hemodynamic performance. The superior hemodynamic performance of the LV cathodes may be determined by comparison of measured values indicative of hemodynamic performance to a threshold value. For example, the LV time delay achieved using the LV cathode electrodes associated with PNA may be required to fall below a predetermined LV time delay threshold and/or the QRS width may be required to fall within a predetermined range, otherwise the LV cathodes are eliminated from further testing. If PNA is present during pacing for all or a predetermined number LV cathodes, then the lead can be repositioned if the testing is occurring during the implant process.

The early elimination sub-process 105 identifies LV cathodes having pacing characteristics that are more desirable than other LV cathodes. The LV cathodes identified by the early elimination sub-process 105 are denoted herein as "viable LV cathodes" with the understanding that LV pacing vectors using these "viable" LV cathodes are more likely to be selected for pacing therapy in subsequent AVT processes. The sub-process 105 eliminates LV cathodes which are not viable (which can be denoted the non-viable LV cathodes) from further testing because LV pacing vectors using these non-viable LV cathodes are unlikely to be selected for LV pacing therapy. Such an early elimination process to eliminate certain LV cathodes and identify others for further testing saves time in the subsequent steps of the AVT process because all LV pacing vectors using the non-viable LV cathodes are eliminated from consideration before a subsequent phase involving more extensive LV vector testing occurs.

After the initial sub-process 105 is complete, a final stage of testing 145 and pacing vector ranking 155 occurs. For the set of viable LV cathodes identified by the early elimination sub-process 105, the LV capture threshold, pacing impedance, and/or PNA threshold (if any) for available LV pacing vector configurations (bipolar, unipolar, and extended bipolar, etc.) for each LV cathode are measured 140. For these LV pacing vectors, the LV cathodes are the viable LV cathodes previously identified. The anode electrodes for these LV pacing vectors may be individual electrodes or may be multiple anode electrodes which are used together.

Only a subset LV pacing vectors, e.g., the most commonly used vector configurations, can be tested if a complete search of all possible vectors for each of the viable LV cathodes is prohibitive or is not desired. A more complete search of the LV pacing vectors may be subsequently performed if it is determined that PNA cannot be avoided or if the cardiac capture thresholds are excessively high using this subset of LV pacing vectors.

During cardiac capture/PNA testing of extended bipolar LV pacing vectors (those pacing vectors that use a right chamber anode), the testing process may include monitoring for anodal stimulation. If anodal stimulation is detected in conjunction with a particular LV pacing vector, then an indication of anodal stimulation is stored along with the pacing voltages at which anodal stimulation occurs. Anodal stimulation may be desirable or undesirable in view of the specific patient's condition.

The ranking sub-process 155 may include a multi-tiered approach, such as a two-tiered ranking table for the potential LV pacing vectors. In one implementation, the LV cathodes are ranked 150 in a first tier according to efficacy of hemodynamic function. In a second tier, each of the LV pacing vectors using that LV cathode is ranked 160 based on the margin between the PNA threshold and the cardiac capture threshold. For example, those LV pacing vectors providing the largest margin between PNA and the cardiac capture threshold may be ranked highest in the second tier, with vectors exhibiting smaller margins between the PNA and cardiac capture thresholds ranked lower. The anodal stimulation detection results may be used in the ranking process, or may simply be reported in the ranking table for any extended bipolar vectors.

Figure 2:
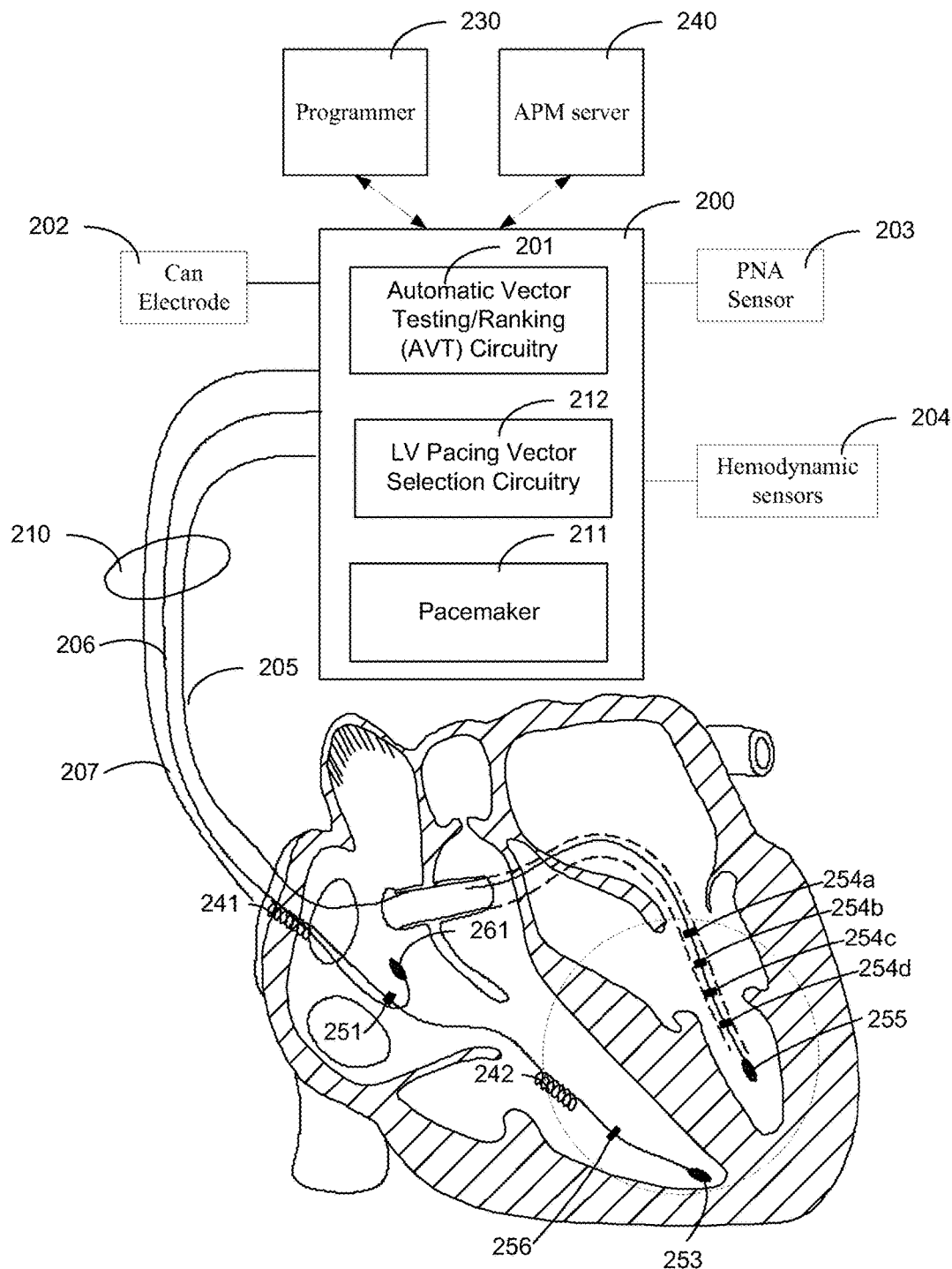
FIG. 2 is a diagram of a medical device employing circuitry capable of implementing the pacing vector testing/ranking processes according to embodiments of the invention.

The medical device 200 illustrated in FIG. 2 employs circuitry capable of implementing the automatic LV pacing vector testing/ranking (AVT) and/or LV pacing vector selection techniques described herein. The medical device 200 includes one or both of AVT circuitry 201 and/or LV pacing vector selection circuitry 212. The AVT circuitry 201 is configured to implement the LV pacing vector testing/ranking (AVT) processes such as those described in FIG. 1. The LV pacing vector selection circuitry 212 is configured to implement the LV pacing vector selection processes as described herein. In one implementation, the medical device is a patient-external pacing system analyzer (PSA) which can be attached to an intracardiac lead system 210 during an implant procedure. In another implementation, the medical device 200 is an implantable cardiac rhythm management (CRM) device, such as a pacemaker, defibrillator, and/or cardiac resynchronizer, with the AVT circuitry 201 and/or LV pacing vector selection circuitry 212 implemented within the housing of the CRM device. In yet another implementation, the medical device 200 comprises a combination of two or more of CRM device, CRM device programmer and an advanced patient management (APM) system.

A lead system 210 extending into the patient's heart is attached to the medical device 200. The intracardiac lead system 210 may include one or more leads 205-207 disposed in, on or about the left ventricle, right ventricle, left atrium and/or right atrium. Each lead 205-207 is coupled to electrodes configured to sense cardiac electrical signals and/or to deliver pacing energy to the heart. In addition, the medical device 200 may be coupled to one or more subcutaneous, non-intracardiac electrodes, such as a can electrode 202. If an implantable CRM device is used, the can electrode 202 is typically positioned on the implantable housing. If a patient-external device is used, the can electrode 202 of a CRM device can be simulated by placement of an electrode positioned in the pectoral region where a CRM device would be implanted and attached by a lead to the medical device 200.

As illustrated in FIG. 2, the lead system 210 includes cardiac pace/sense electrodes 251-256 positioned in, on, or about one or more heart chambers for sensing electrical signals from the patient's heart and/or delivering pacing pulses to the heart. The intracardiac sense/pace electrodes 251-256, may be used to sense and/or pace one or more chambers of the heart, including the left ventricle, the right ventricle, the left atrium and/or the right atrium. The medical device 200 may incorporate pacemaker circuitry 211 which controls the delivery of pacing pulses to the heart via the pace/sense electrodes 251-256.

The lead system 210 may include defibrillation electrodes 241, 242 for delivering defibrillation/cardioversion pulses to the heart. The defibrillation electrodes 241, 242 may be used as pacing and/or sensing electrodes and/or may be coupled to an evoked response channel (not shown in this diagram) for detection of cardiac capture.

As illustrated in FIG. 2, the left ventricular lead 205 incorporates multiple electrodes 254a-254d and 255 positioned at various locations within the coronary venous system proximate the left ventricle. Stimulating the ventricle at one or more selected locations in the left ventricle may provide for increased cardiac output in a patients suffering from congestive heart failure (CHF), for example, and/or may provide for other benefits. Electrical stimulation pulses may be delivered via the selected electrodes according to a timing sequence and output configuration that enhances cardiac function. Similarly to the configuration shown in the left ventricle in FIG. 2, multiple electrodes may be deployed in one or more of the right atrium, left atrium, left ventricle and right ventricle.

The medical device 200 is also coupled to various sensors for use in the AVT process including a sensor 203 configured to detect phrenic nerve activation (PNA). For example, an accelerometer and/or a respiration sensor may be used to detect PNA. For patient-external PNA sensing, the PNA sensor, e.g., accelerometer or other motion sensor, may be externally mounted on the patient at a location suitable for detecting the "hiccup" type movement of the diaphragm that occurs when PNA occurs. For implantable implementations, the PNA sensor may comprise an accelerometer disposed within the implantable housing of the CRM device, and/or may comprise a respiration sensor and appropriate circuitry configured to detect the hiccup response in the respiration signal.

The medical device 200 may also be coupled to one or more sensors 204 for sensing hemodynamic parameters. In some configuration, the hemodynamic testing step described above is performed by sensing the cardiac electrogram and measuring timing intervals from the sensed cardiac electrogram, e.g., LV timing delay and/or QRS width. Hemodynamic function testing may be performed using a pressure sensor to measure LV dp/dt, and/or a cardiac wall motion sensor configured to detect ventricular dyssynchrony. Other types of sensors useful for hemodynamic function testing include, for example, pressure catheters in any chamber or the heart, in the pulmonary artery, arterial pressure, non-invasive sensors such as heart sounds based measurements, echocardiographic techniques, fluoroscopic measurements, finger plethysmography, and/or other types of sensors.

The medical device 200 may be coupled to one or both of a programmer 230 and an automatic patient management system 240. In some configurations, the AVT circuitry 201 and/or LV pacing vector selection circuitry 212 may be operated under the program control of the device programmer 230 and/or the APM system 240. In other configurations, the AVT circuitry 201 and/or LV pacing vector selection circuitry 212 may operate independently of either the programmer 230 or the APM system 240

Figure 3:
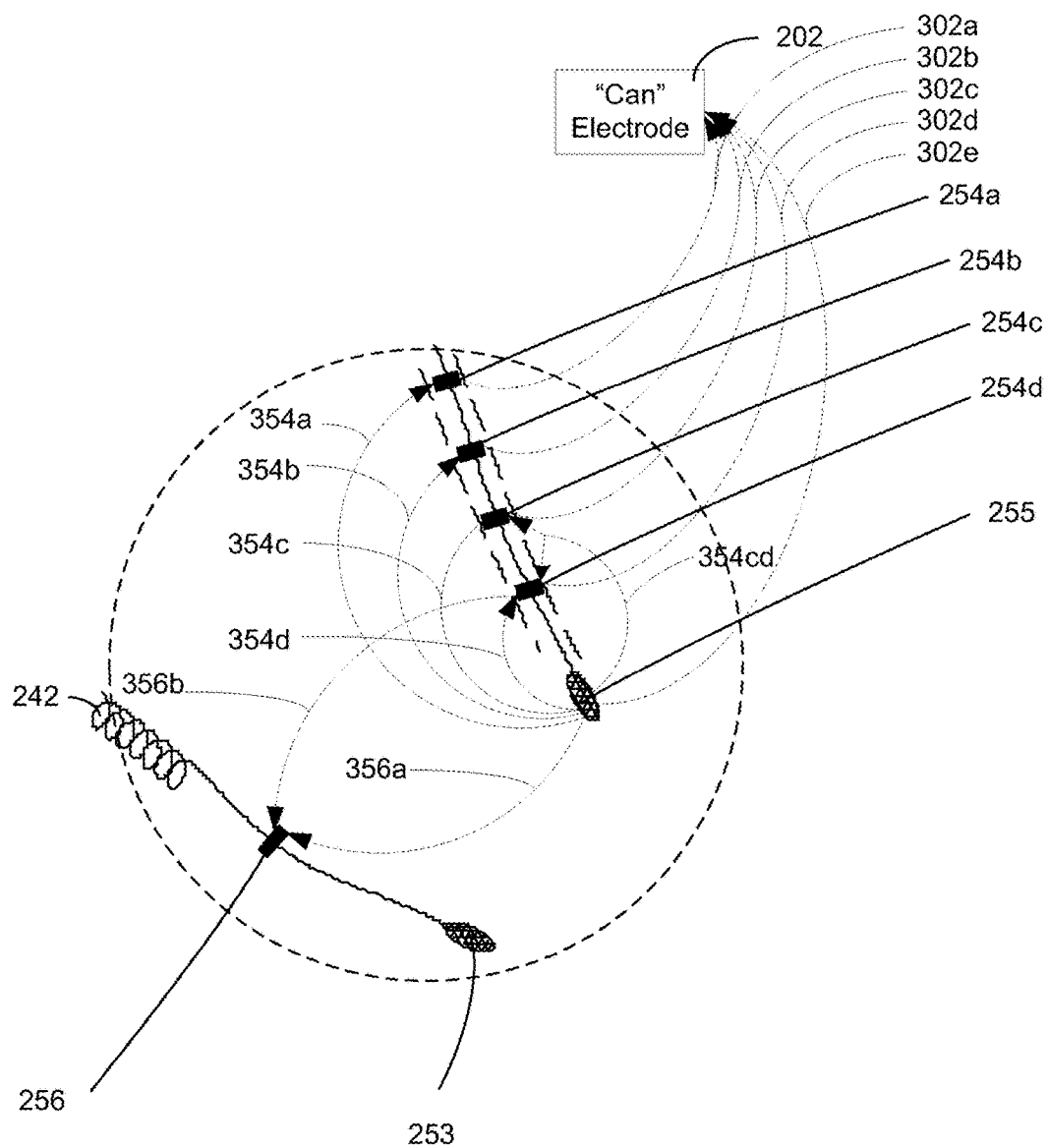
FIG. 3 shows an enlarged view of various LV pacing vectors that may be tested and ranked in accordance with various embodiments of the invention.

FIG. 3 illustrates an enlarged view of the area delineated by the dashed line circle in FIG. 2. FIG. 3 illustrates various LV pacing vectors between a cathode and an anode, wherein the vector direction is defined as cathode to anode. FIG. 3 depicts bipolar LV pacing vectors 354a, 354b, 354c, 354d, 354cd; extended bipolar LV pacing vectors 356a and 356b; and unipolar LV pacing vectors 302a, 302b, 302c, 302d, and 302e. Not all possible LV pacing vector configurations are illustrated in FIG. 3, due to the large number of possible combinations. Any one or more of the LV electrodes 245a-d and 255 may be used as an LV cathode with any one or more of the remaining electrodes 245a-d, 255, 253, 256, 242 used as an anode. Thus, the LV pacing vectors 354a, 354b, 354c, 354d, 354cd, 356a, 356b, 302a, 302b, 302c, 302d, and 302e illustrated in FIG. 3 provide an exemplary rather than an exhaustive depiction of possible LV pacing vectors.

Each of the bipolar LV pacing vectors 354a, 354b, 354c, 354d, and 354cd illustrated in FIG. 3 includes a common cathode electrode 255. Pacing vector 354a is defined between cathode electrode 255 and anode electrode 254a; pacing vector 354b is defined between cathode electrode 255 and anode electrode 254b; pacing vector 354c is defined between cathode electrode 255 and anode electrode 254c; pacing configuration 354d is defined between cathode electrode 255 and anode electrode 254d; pacing configuration 356 is defined between cathode electrode 255 and anode electrode 656. In some configurations, the pacing configuration cathode, or the pacing configuration anode, or both, may comprise multiple electrodes. For example, pacing configuration 354cd includes cathode electrode 255 and anode electrodes 254c and 254d.

Each of the unipolar LV pacing vectors 302a-e illustrated in FIG. 3 show the can electrode as the anode. Pacing vector 302a is defined between cathode electrode 254a and the can 202; pacing vector 302b is defined between cathode electrode 254b and the can 202; Pacing vector 302c is defined between cathode electrode 254c and the can 202; pacing vector 302d is defined between cathode electrode 254d and the can 202; and pacing vector 302*e* is defined between cathode electrode 255 and the can 202.

FIG. 3 illustrates two extended bipolar vectors 356*a*, 356*b*. Pacing vector 356*a* is defined between cathode electrode 255 and the RV ring electrode 256; pacing vector 356*b* is defined between cathode electrode 354*d* and the RV ring electrode 256. Although not shown for every combination, the bipolar, unipolar and/or extended bipolar electrodes may each use multiple electrodes as the cathode and/or multiple electrodes as the anode.

Figure 4A:
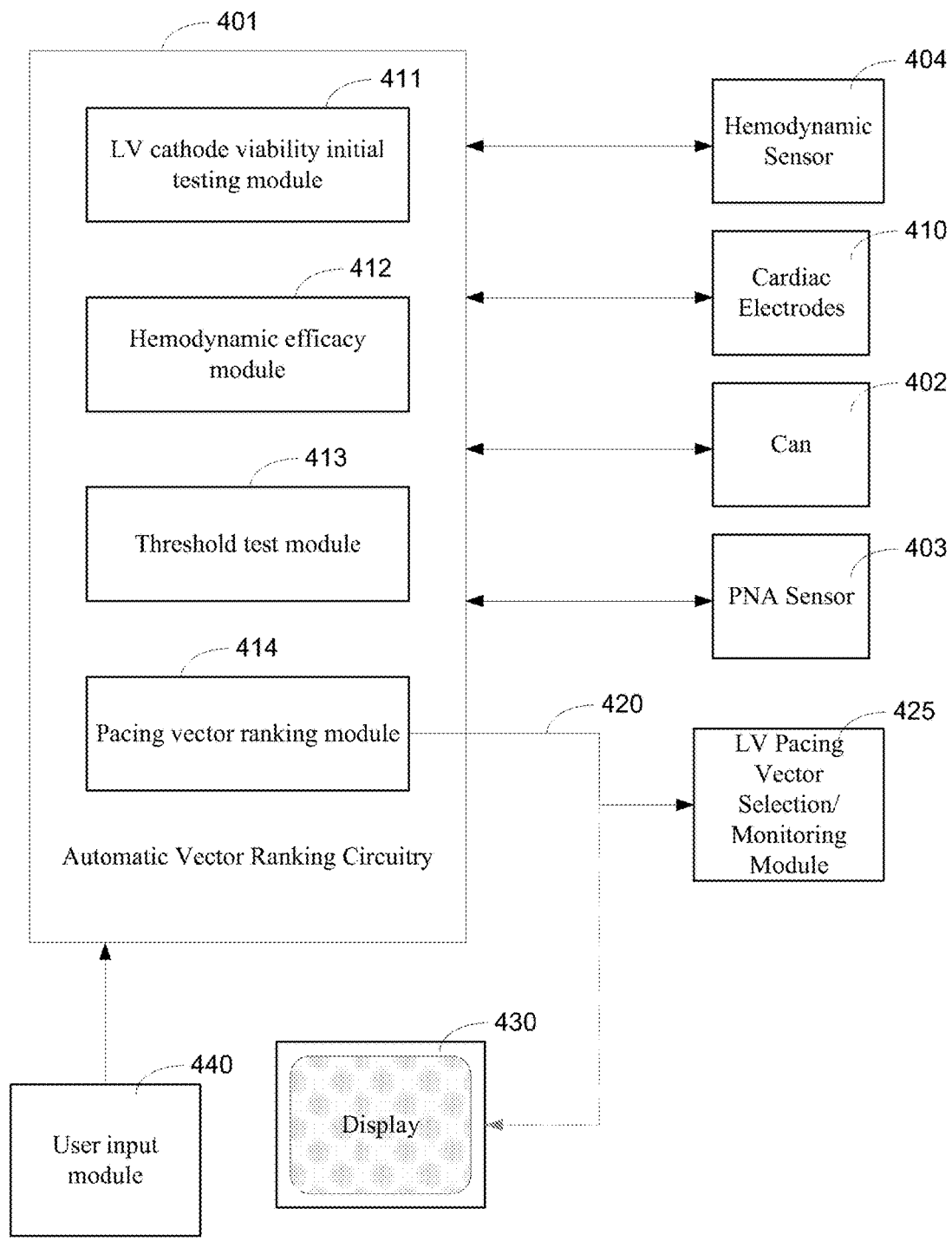
FIG. 4A is a block diagram of a medical device that may be used to implement pacing vector testing, ranking, selection and/or monitoring in accordance with embodiments of the invention.

FIG. 4A depicts a functional block diagram of circuitry and devices used in connection with automatic LV pacing vector testing and ranking (AVT) and LV pacing vector selection in accordance with embodiments of the invention. The automatic LV pacing vector testing and ranking (AVT) circuitry 401 includes various circuitry modules 411-414 for carrying out the processes of vector testing and ranking as described herein. The functions of AVT processes may be carried out using any combination of hardware or software, including embodiments implemented fully by hardware components, and embodiments implemented by microprocessor-based circuitry executing firmware or software program instructions stored in memory. The AVT circuitry 401 is coupled to various sensors including the implantable cardiac electrodes 410, can electrode 402, one or more hemodynamic sensors 404, and one or more PNA sensors 403 as previously described.

The AVT circuitry 401 includes a pacing electrode viability module that is configured to perform the early elimination pacing electrode viability processes as described, for example in connection with blocks 110-120 of FIG. 1. The pacing viability module 411 implements one or more tests to identify LV cathodes that are used in further testing. After testing, the pacing viability module 411 identifies a subset of LV cathode electrodes for the next phase of early elimination testing. For example, the pacing viability module 411 may compare the results of measured intrinsic or paced values for each tested LV cathode to an expected range. If the results of the measured values for a particular LV cathode fall outside of an expected range, the cathode eliminated from further testing. For example, the initial testing module 411 may implement cardiac capture testing using a limited subset of testing voltages If a particular LV cathode does not produce capture at the limited subset of testing voltages, and/or if the capture threshold for pacing using the LV cathode is beyond an expected range, then the initial testing module cathode 411 may be eliminate the LV cathode from further testing. Alternatively, or additionally, testing based on other measured pacing characteristics, e.g., hemodynamics, phrenic nerve activation, may be used by the initial testing module 411 to eliminate LV cathodes from the testing process.

A hemodynamic efficacy module 412 is configured to carry out the processes described in connection with block 130 of FIG. 1, for example. The hemodynamic efficacy module 412 tests a subset of LV cathodes to determine hemodynamic differences between the these LV cathodes. In some embodiments, the hemodynamic differences may be identified using sensed LV time delay methods. As previously discussed, some LV cathodes may not be tested in this sub-process, e.g., only one or a few of the LV cathode electrodes that are within a predetermined distance of each other may be tested. For LV cathode electrodes within a predetermined distance of each other, it may be assumed that the hemodynamic differences would be inconsequential or that the values can be extrapolated or interpolated from the results of other LV cathodes, and testing for these LV cathodes may be skipped in the interest of test time efficiency.

The time interval between the reference event and a depolarization detected at the LV cathode under test may be measured as the sensed LV time delay. If one or more hemodynamically preferable cathode electrodes are identified by the hemodynamic efficacy module 412, the presence of low phrenic nerve activation (PNA) threshold and/or high cardiac capture threshold will not necessarily eliminate the hemodynamically preferable cathode electrodes from consideration by subsequent modules.

The threshold test module 413 performs operations involving cardiac capture testing, PNA testing, and anodal stimulation threshold testing (140 of FIG. 1). For LV pacing vectors remaining under consideration after the early elimination of non-viable LV cathodes, the LV cardiac capture threshold, anodal stimulation threshold (if any), and/or PNA threshold (if any) for all available vector configurations (bipolar, unipolar, extended bipolar, etc.) for LV cathodes are measured by the threshold test module 413. A reduced set of most commonly used LV pacing vector configurations can be used if a complete search of all possible LV pacing vectors is not desired. A more complete search may be performed if PNA or anodal stimulation cannot be avoided or if the cardiac capture thresholds are excessively high for each of the reduced set of vector configurations, for example.

During cardiac capture/PNA testing of biplor pacing vectors (those pacing vectors that use an RV anode), threshold test module monitors for anodal stimulation. If anodal stimulation is detected in conjunction with a particular pacing vector, then an indication of anodal stimulation is stored along with the pacing voltages at which anodal stimulation occurs.

The vector ranking module 414 inputs the test information acquired by the other modules 411-413, and, optionally, physician input entered via a user input module 440, and ranks the potential LV pacing vectors as described, for example, in connection with blocks 150 and 160 of FIG. 1. The ranking sub-process (155 of FIG. 1) may include a two-tiered approach. In one implementation, the LV cathodes are ranked by the vector ranking module 414 in a first tier according to efficacy of hemodynamic function. In a second tier, the vector ranking module 414 ranks each of the vectors using that LV cathode based on the largest margin between the PNA threshold and the cardiac capture threshold. The vector ranking module 414 develops a LV pacing vector ranking table that is stored in memory for later access. The anodal stimulation detection results may also be included in the ranking table for any extended bipolar vectors. The LV pacing vector ranking module 414 generates an output signal 420 based on the LV pacing vector ranking. The output signal 420 may be used to control an output device 430, such as a display, that presents LV pacing vector selection recommendations to a physician. In another implementation, the output signal 420 may be used as an input to an automatic vector selection module 425 implemented by a CRM device or other device that causes the CRM device to switch from one LV pacing vector to another LV pacing vector.

The user input module 440 allows the physician to input various parameters associated with the AVT and/or LV pacing vector selection process. For example, via the input module 440, the physician may input one or more priority factors for use in ranking or re-ranking the potential LV pacing vectors. In one scenario, the physician may initially select absence of PNA as a primary factor to be used in the ranking. At a later time, the physician may select hemodynamic efficacy as a primary factor, indicating that an absence of PNA is less important that hemodynamic efficacy. If the potential LV pacing vectors have already been ranked, a change in the priority factors may cause the potential LV pacing vectors to be re-ranked based on the changed priority factors.

The physician may choose one or more desired LV pacing vector configuration(s) according to their preferences for the patient, e.g., hemodynamic benefit vs. PNA avoidance, etc.) In another example, the physician may enter variables that control the vector ranking process. The physician may override a recommendation that is displayed and/or may rearrange the rank order either manually, or by changing the variables of priority.

Additionally or alternatively, a physician may chose to enable the LV pacing vector selection module 425 to allow automatic LV pacing vector selection by the device. The CRM device may switch LV pacing vectors if PNA is detected, if cardiac capture is lost, if the pacing threshold becomes too high, or if the hemodynamic benefit of the pacing vector declines, or for other reasons. The LV pacing vector selection module 425 accesses the ranking table produced by the pacing vector ranking module 414 to determine the order in which alternate LV pacing vectors will be selected. The CRM device may notify the physician via an APM system that the alternate LV pacing vector has been selected. If automatic vector switching is enabled, the LV pacing vectors may be subjected to additional testing in the rank order of the table. If a LV pacing vector does not perform acceptably in this additional testing, it is discarded and the next ranked LV pacing vector is selected and tested.

In some configurations, the physician may select ambulatory LV pacing vector monitoring. In this capacity, LV pacing vectors of interest are selected based on the rank order of the table developed by the ranking module 414. The selected LV pacing vectors are automatically tested periodically. The tests involved may include one or more of cardiac capture threshold, PNA threshold, presence and/or threshold for anodal stimulation, intrinsic measurements such as impedance and R-wave amplitude. The resulting metrics can be stored and trended for later review.

Figure 4B:
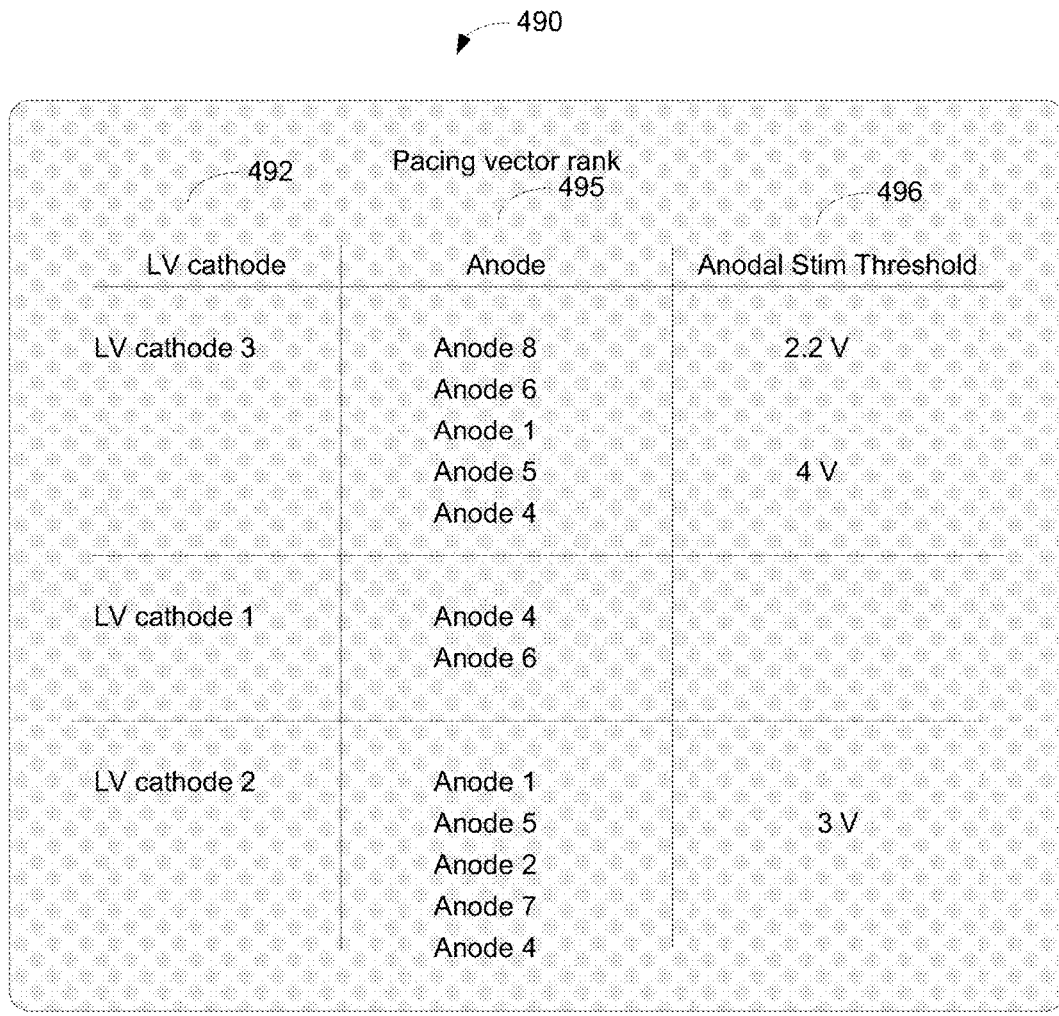
FIG. 4B illustrates an exemplary ranking hierarchy for pacing vectors in accordance with embodiments of the invention.

FIG. 4B illustrates a ranking hierarchy 490 that may be utilized by the ranking module 414. In some implementations ranking hierarchy 490 illustrated by FIG. 4B may be generated on the display 430 in some form for review by a physician. The ranking hierarchy 490 includes a first tier 492 which ranks the LV cathodes based on the measured value of hemodynamic function. The ranking hierarchy 490 also includes a second tier 495 which ranks potential pacing vectors which use the LV cathode ranked in the first tier 492. For example, the first tier 492 ranks LV cathode 3 as the highest cathode and the second tier 495 ranks the following pacing vectors: LV cathode 3→Anode 8, LV cathode 3→Anode 6, LV cathode 3→Anode 1, LV cathode 3→Anode 5, LV cathode 3→Anode 4, all of which use LV cathode 3 as the pacing vector cathode. Anodal stimulation information 496 may optionally be stored and/or displayed along with pacing vector ranking information.

For ischemic cardiomyopathy patients, pacing the near the infarct could be problematic with respect to high threshold values, slower propagation or cardiac signals, etc, particularly for pacing in the LV. Therefore, with a multiple electrode lead, pacing site selection may be used to improve the response in such patients.

Pacing vector ranking and selection circuitry may be configured to take into account the proximity of an electrode to an infarct site. Electrodes used as cathode or anode electrodes for the pacing vector may be eliminated by in the early elimination sub-process or subsequent ranking sub-processes of the AVT algorithm based on the proximity of the electrode to an infarct site. The proximity of an electrode to the infarct site may be determined based measured signal amplitudes and cardiac capture thresholds. A group of electrodes having similar measured signal amplitudes are assumed to have comparable electrode contact with the cardiac tissue. Therefore, electrodes of this group which have higher cardiac capture thresholds than other electrodes of the group are identified as being near or above the infarct region. Pacing vectors using these electrodes may be eliminated, e.g., by the ranking module (414, FIG. 4A), from those ranked for use as pacing vectors.

Electrodes determined to be near the infarct region may be flagged and tracked for reporting or diagnostic purposes. Such electrodes can also be excluded for use in making hemodynamic measures, such as LV timing intervals including Q-LV timing.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A medical system, comprising:
   a plurality of cardiac electrodes configured to be electrically coupled to a heart;
   a hemodynamic function circuit configured to measure a parameter value indicative of hemodynamic function for a selected plurality of cardiac electrodes as potential Left Ventricular (LV) pacing vectors;
   a pacing viability circuit configured to eliminate one or more of the selected plurality of cardiac electrodes from a set of viable cardiac electrodes according to the parameter indicating hemodynamic function;
   a threshold test circuit configured to measure one or both of a cardiac capture threshold and a phrenic nerve activation threshold for the set of viable cardiac electrodes;
   a ranking circuit configured to rank at least some of the potential LV pacing vectors based on the value of the hemodynamic function parameter and the one or both of the measured capture threshold and the phrenic nerve activation threshold.

2. The medical system of claim 1, including an input circuit configured to receive input utilized at least in part for selection from a plurality of measured parameter values and threshold measurements for priority in ranking potential LV pacing vectors,
   wherein the ranking circuit is configured to rank at least some of the potential LV pacing vectors based on the value of the hemodynamic function parameter, the one or both of the measured capture threshold and the phrenic nerve activation threshold, and the priority input.

3. The medical system of claim 1, wherein the pacing viability circuit is configured to measure one or more parameter values for a plurality of cardiac electrodes and to identify each of the plurality of cardiac electrodes as a viable cardiac electrode or an eliminated cardiac electrode based on the one or more measured parameter values for that particular cardiac electrode, the viable cardiac electrodes subject to further testing and the eliminated cardiac electrodes eliminated from further testing.

4. The medical system of claim 1, wherein the ranking circuit is further configured to identify one or more cardiac electrodes that are within an infarct region based on signal amplitudes and the capture thresholds of the identified cardiac electrodes and to eliminate from the ranking potential LV pacing vectors that use one or more cardiac electrodes near the infarct region.

5. The medical system of claim 1, wherein the hemodynamic function circuit, the threshold test circuit and the ranking circuit are disposed outside of a patient's body in a patient-external pacing system analyzer.

6. The medical system of claim 5, further comprising an accelerometer configured to be attached to an external portion of the patient's body and to sense movement indicative of phrenic nerve activation.

7. The medical system of claim 5, further comprising a subcutaneous electrode disposed on a lead that simulates a can electrode of a cardiac rhythm management device.

8. The medical system of claim 1, wherein the hemodynamic function circuit, the threshold test circuit and the ranking circuit are disposed within a housing of an implantable cardiac device.

9. A cardiac system for ranking potential Left Ventricular (LV) pacing vectors, comprising:
   an input circuit configured to receive input utilized at least in part for one or both of a selection of a plurality of cardiac electrodes for testing as potential LV pacing vectors and selection from a plurality of measurable parameter values and threshold measurements for priority in ranking the potential LV pacing vectors;
   a hemodynamic function circuit configured to measure a parameter value indicative of hemodynamic function for the selected plurality of cardiac electrodes;
   a pacing viability circuit configured to eliminate one or more of the selected plurality of cardiac electrodes from a set of viable cardiac electrodes according to the parameter indicating hemodynamic function;
   a threshold test circuit configured to measure one or both of a cardiac capture threshold and a phrenic nerve activation threshold for the set of viable cardiac electrodes;
   a ranking circuit configured to rank at least some of the potential LV pacing vectors based at least in part on each of the values of the hemodynamic function parameter, the one or both of the measured capture threshold and the phrenic nerve activation threshold, and the priority input; and
   the ranking circuit further configured to provide an output based on the ranking.

10. The cardiac system of claim 9, further comprising a user interface configured to:
    display one or both of text and graphics identifying the potential LV pacing vectors in an order that is based on the ranking;
    receive input of a different selection of the plurality of cardiac electrodes for testing as potential LV pacing vectors; and
    receive input indicating a different priority for parameter values and threshold measurements used to rank the potential LV pacing vectors.

11. The cardiac system of claim 10, wherein the ranking circuit is further configured to re-rank the potential LV pacing vectors based at least in part on one or both of the different selection of the cardiac electrodes for testing and the different ranking priority.

12. The medical system of claim 9, wherein the pacing viability circuit is configured to measure one or more parameter values for a plurality of cardiac electrodes and to identify each of the plurality of cardiac electrodes as a viable cardiac electrode or an eliminated cardiac electrode based on the one or more measured parameter values for that particular cardiac electrode, the viable cardiac electrodes subject to further testing and the eliminated cardiac electrodes eliminated from further testing.

13. The medical system of claim 9, wherein the ranking circuit is further configured to identify one or more cardiac electrodes that are within an infarct region based on signal amplitudes and the capture thresholds of the identified cardiac electrodes and to eliminate from the ranking potential LV pacing vectors that use one or more cardiac electrodes near the infarct region.

14. The medical system of claim 9, wherein the hemodynamic function circuit, the threshold test circuit and the ranking circuit are disposed outside of a patient's body in a patient-external pacing system analyzer.

15. The medical system of claim 14, further comprising an accelerometer configured to be attached to an external portion of the patient's body and to sense movement indicative of phrenic nerve activation.

16. The medical system of claim 14, further comprising a subcutaneous electrode disposed on a lead that simulates a can electrode of a cardiac rhythm management device.

17. The medical system of claim 9, wherein the hemodynamic function circuit, the threshold test circuit and the ranking circuit are disposed within a housing of an implantable cardiac device.

18. A medical system, comprising:
    means for receiving input utilized for, at least in part, a selection of a plurality of cardiac electrodes for testing as potential Left Ventricular (LV) pacing vectors;
    means for measuring a value of a parameter indicating hemodynamic function of pacing for the selected plurality of cardiac electrodes;
    means for eliminating one or more cardiac electrodes from a set of viable cardiac electrodes according to the parameter indicating hemodynamic function, wherein further testing is performed only on the set of viable cardiac electrodes;
    means for measuring one or both of a cardiac capture threshold and a phrenic nerve activation threshold for the set of viable cardiac electrodes; and
    means for ranking at least some of the potential LV pacing vectors based on the value of the hemodynamic function parameter and the one or both of the measured capture threshold and the phrenic nerve activation threshold.

19. The medical system of claim 18, including:
    means for ranking potential LV pacing vectors in a first tier and one or more additional tiers, at least one tier ranking viable LV cardiac electrodes based on the measured value of the hemodynamic function parameter and at least another tier ranking the potential LV pacing vectors based on a difference between the cardiac capture threshold and the phrenic nerve activation threshold.

20. The medical system of claim 18, including:
means for identifying a set of hemodynamically preferred cardiac electrodes from the viable cardiac electrodes based on the measured value of the hemodynamic function parameter;
means for delivering pacing using at least some of the viable cardiac electrodes;
means for monitoring for phrenic nerve activation caused by the pacing; and
means for eliminating from further consideration each cardiac electrode of the viable cardiac electrodes that is associated with phrenic nerve activation and which is not included in the set of hemodynamically preferred cardiac electrodes.

* * * * *